United States Patent [19]
Weyer et al.

[11] Patent Number: 5,824,769
[45] Date of Patent: Oct. 20, 1998

[54] POLYETHER, POLYESTER AND POLYETHER ESTER PURIFICATION PROCESS

[75] Inventors: Hans-Jürgen Weyer, Bobenheim-Roxheim; Rolf Fischer, Heidelberg, both of Germany

[73] Assignee: BASF Aktiengesellschaft, Ludwigshafen, Germany

[21] Appl. No.: 809,690

[22] PCT Filed: Oct. 6, 1995

[86] PCT No.: PCT/EP95/03957

§ 371 Date: Aug. 4, 1997

§ 102(e) Date: Aug. 4, 1997

[87] PCT Pub. No.: WO96/11223

PCT Pub. Date: Apr. 18, 1996

[30] Foreign Application Priority Data

Oct. 7, 1994 [DE] Germany ............ 44 35 930.6
Feb. 20, 1995 [DE] Germany ............ 195 05 705.8

[51] Int. Cl.⁶ ................................. C08F 6/00
[52] U.S. Cl. ............ 528/485; 528/482; 528/487; 528/488; 528/489; 528/490; 528/491; 528/502; 528/503; 210/767; 210/768
[58] Field of Search .................. 528/482, 485, 528/487, 488, 489, 490, 491, 502, 503; 210/767, 768

[56] References Cited

U.S. PATENT DOCUMENTS 4,677,231 6/1987 Aoshima et al. ............ 568/617
5,414,143 5/1995 Weyer et al. ............ 568/617

FOREIGN PATENT DOCUMENTS 000 944  3/1979   European Pat. Off. .
126471   11/1984  European Pat. Off. .
158229   10/1985  European Pat. Off. .
181 621  5/1986   European Pat. Off. .
503 394  9/1992   European Pat. Off. .
8083028  11/1981  Japan .
61-200120 3/1985  Japan .
1754732  11/1989  U.S.S.R. .
1369304  10/1974  United Kingdom .

*Primary Examiner*—Samuel A. Acquah
*Attorney, Agent, or Firm*—Keil & Weinkauf

[57] ABSTRACT

A process is described for removing heteropoly compounds from heteropoly compound-contaminated polyethers, polyesters and/or polyether esters, which comprises admixing the polymer or a solution of the same with a compound which contains at least one heteroatom which is selected from the group consisting of central atoms of heteropolyacids, is non-protic and is of a polarity so low that its addition leads to the heteropoly compounds separating out in a separate phase, and separating off the precipitated heteropoly compound phase. The remaining polymer phase is preferably further purified using a solid adsorbent.

12 Claims, No Drawings

POLYETHER, POLYESTER AND POLYETHER ESTER PURIFICATION PROCESS

The invention relates to a process for purifying heteropoly compound-containing polyethers, polyesters and polyether esters or their solutions by mixing the same with a compound which contains at least one heteroatom, which can be present as the central atom of a heteropolymer compound, is non-protic and is of a polarity so low that its addition leads to the separation of the heteropolymer compound in a separate phase.

Polyethers, polyesters and polyether esters are used in many ways; examples are their use in hydraulic oils or as diol component in the preparation of polyurethanes. These compounds are prepared by cationic polymerization or copolymerization of corresponding monomers, for example cyclic ethers, acetates, polyalcohols or lactones, using Brönsted acid or Lewis acid catalysts. Heteropolyacids and heteropolyacid salts, jointly termed "heteropoly compound(s)" or "HPA" below, have proved to be particularly advantageous catalysts for ring-opening polymerization. To establish the desired polymer molar mass and/or to prepare special end-group-modified derivatives, substances are customarily present in the polymerization whose inclusion leads directly or indirectly to chain termination. Examples of these are carboxylic acid derivatives, alcohols or water.

JP-A-33 028/1983 describes, for example, the polymerization of tetrahydrofuran (THF) in the presence of a carboxylic anhydride or carboxylic acid halide with the formation of polyTHF diesters, a heteropolyacid being used as catalyst.

EP 126 471 teaches the HPA-catalyzed polymerization of THF and the copolymerization of THF with various other cyclic ethers in the presence of water, with the formation of poly(ether glycols). EP 158 229 describes the preparation of poly(ether glycols) by copolymerization of cyclic ethers with di- and higher-functional alcohols.

According to JP 61-200120, lactones, or lactones together with cyclic ethers, can be polymerized in the presence of hydroxyl-containing compounds with heteropolyacids as catalysts.

Poly(ether glycol)monoethers and poly(ether glycol) monoesters may be prepared according to EP 503 393 and EP 503 394 by polymerizing cyclic ethers in the presence of monoalcohols or monocarboxylic acids with HPA catalysts.

In these polymerization processes for preparing polyethers, polyesters and polyether esters, polymer phases are formed which, on account of the incomplete conversion, still contain residual amounts of monomer(s) residual amounts of the compound(s) leading to chain termination, any solvents used, and also dissolved heteropoly compound(s). The percentage of HPA catalyst dissolved in the polymer phase is considerable in these reactions and can be up to 1% by weight or more, based on the polymer phase. The dissolved catalyst does not precipitate out in the event of a separation which merely consists of distilling off unreacted monomer, chain-termination reagent(s), and any solvent used, from this phase, but remains in dissolved form in the polymer. On the one hand, this must be prevented for quality reasons, and on the other hand it is desirable for reasons of costs, since heteropolyacids are very expensive, to recover the majority of the catalyst.

It is further known that heteropoly compounds decompose in the course of time, more intensively under thermal stress. This occurs principally by hydrolysis, with formation of the corresponding oxides. The decomposition of heteropoly compounds can be decreased or completely prevented if compounds are added which contain elements which can occur as central atoms in heteropoly compounds. For example, the hydrolytic stability of phosphorus poly acids is markedly increased in the presence of phosphoric acid (A. Aoshima, S. Yamamatsu, T. Yamaguchi, Nippon Kagaku Kaishi, (1990) 233). The hydrolytic stability of HPA is likewise increased under reducing conditions (M. T. Pope, E. Papaconstantinou, Inorg. Chem. 6 (1967) 1147).

To solve the problem of separating off heteropoly compounds, it is proposed in EP 181 621 to add a hydrocarbon or halogenated hydrocarbon to the polymer phase, as a result of which the majority of the dissolved heteropolyacid precipitates out and/or separates out as a separate phase. The separated hydrocarbon/polymer phase is then treated with a solid adsorbent. However, stabilization of the heteropoly compounds by precipitation with a halogenated or non-halogenated hydrocarbon is not achieved in this process.

In SU 1754732 A1, after concentrating the polymer phase to 50-90% polymer, a hydrocarbon having 1–15 carbon atoms is likewise added to precipitate out the heteropoly compound. However, instead of a further purification by adsorption, a liquid organic nitrogen base is then added which forms an insoluble salt with heteropoly compound still present, which must be the acid in this case, which salt precipitates out and can be separated off in a conventional manner. However, the purity which can be achieved in this manner of approximately $50 \times 10^{-6}\%$ heteropoly compound in the polymer is not adequate for most purposes.

It is an object of the present invention, therefore, to provide a process for purifying heteropoly compound-containing polyethers, polyesters and polyether esters or solutions of the same which can separate off heteropoly compounds and at the same time can serve to stabilize the HPA used.

We have found that this object is achieved by a process for removing heteropoly compounds from heteropoly compound-contaminated polyethers, polyesters and/or polyether esters, which comprises mixing these polymers or a solution of the same with a compound which contains at least one heteroelement which is selected from the group consisting of central atoms of heteropolyacids, is non-protic and is of a polarity so low that its addition leads to the precipitation of the heteropoly compound.

Polyethers, polyesters and/or polyether esters can be freed from heteropoly compound(s) by the process according to the invention.

The purification process described can be used for any mixture which comprises HPA and polymers of this type.

Said polymeric compounds can, for example, be made up of monomers of the group consisting of the cyclic ethers, acetals, diols, higher alcohols and lactones. However, it is also possible to free polymeric compounds comprising other monomers from dissolved heteropoly compounds by the process according to the invention. The molar mass of the polyethers, polyesters and/or polyether esters to be purified is not restricted, but is preferably below 5000.

The polyethers, polyesters and/or polyether esters containing the heteropoly compound(s) are used as such or in dissolved form, for example and preferably in their solution arising in the polymerization. In this description and in the claims, a phase which contains at least one of the above polymers is termed "polymer phase" or "(polymer) mixture", whereas a phase which additionally contains a low-molecular weight organic component acting as solvent is termed a "polymer solution".

The polymerization process itself is not of particular importance for the purification according to the invention of polyethers, polyesters and/or polyether esters. The polymerization can be carried out continuously or batchwise and the polymerization system can be, for example, single-phase, two-phase or heterogeneous.

Generally, the polymer solution formed in the polymerization still contains a considerable proportion of monomer(s), a large amount of the chain termination reagent(s) initially added and dissolved heteropoly compound(s). Since it can be advantageous to carry out the polymerization in the presence of a solvent, the polymerization system may also contain such a solvent.

In a preferred polymerization process using HPA catalysis, the procedure is carried out in such a manner that a polymerization mixture having two liquid phases is formed, the one phase being the catalyst phase and the other being the monomer/polymer phase. A typical monomer/polymer phase as formed, for example, in the ring-opening polymerization of THF to give polytetrahydrofuran (PolyTHF) in the presence of water using $H_3PW_{12}O_{40}$ as catalyst in a two-phase polymerization system, has the following composition (figures in % by weight): 77.3% THF, 21.2% PolyTHF, 1.2% $H_3PW_{12}O_{40}$, 0.3% water.

The composition of the polymer phase which is used for the process according to the invention accordingly depends on the type of the catalyst, the monomer or monomers, the chain termination reagent(s) and on the content of solvent which may have been used and is not critical for the process.

According to the novel process, to purify the HPA-containing polymers, compounds are added which contain at least one heteroatom which can occur as central atom in heteropoly compounds, are non-protic and are of a polarity so low that their addition leads to the precipitation of the dissolved heteropoly compound(s).

For the purposes of the present invention, heteropolyacids are inorganic poly acids which have at least two different central atoms and are formed as mixed, partial anhydrides from weak, polybasic oxygen acids of a metal, preferably from those of chromium, molybdenum, vanadium and tungsten, and/or the corresponding oxides of these metals, for example $CrO_3$, $MoO_3$, $V_2O_5$ or $WO_3$, and those of another metal or nonmetal, for example arsenic, boron, iodine, phosphorus, selenium, silicon, germanium, or tellurium. Generally, the atomic ratio of the former to the latter elements in these heteropolyacids is from 2.5 to 12, preferably 9 or 12.

Examples of heteropolyacids which can be removed from the process according to the invention are the following compounds:

dodecamolybdatophosphoric acid ($H_3PMo_{12}O_{40} \cdot nH_2O$),
dodecamolybdatosilicic acid ($H_4SiMo_{12}O_{40} \cdot nH_2O$),
dodecamolybdatoceric(IV) acid ($H_8CeMo_{12}O_{40} \cdot nH_2O$),
dodecamolybdatoarsenic(V) acid ($H_3AsMo_{12}O_{40} \cdot nH_2O$),
hexamolybdatochromic(III) acid ($H_3CrMo_6O_{24}H_6 \cdot nH_2O$),
hexamolybdatonickelic(II) acid ($H_4NiMo_6O_{24}H_6 \cdot 5H_2O$),
hexamolybdatoiodic acid ($H_5IMo_6O_{24} \cdot nH_2O$),
octadecamolybdatodiphosphoric acid ($H_6P_2Mo_{18}O_{62} \cdot 11H_2O$),
octadecamolybdatodiarsenic(V) acid ($H_6As_2Mo_{18}O_{62} \cdot 25H_2O$),
nonamolybdatomanganic(IV) acid ($H_6MnMo_9O_{32} \cdot nH_2O$),
undecamolybdatovanadatophosphoric acid ($H_4PMo_{11}VO_{40} \cdot nH_2O$),
decamolybdatodivanadatophosphoric acid ($H_5PMo_{10}V_2O_{40} \cdot nH_2O$),
dodecavanadatophosphoric acid ($H_7PV_{12}O_{36} \cdot nH_2O$),
dodecatungstosilicic acid ($H_4SiW_{12}O_{40} \cdot 7H_2O$),
dodecatungstophosphoric acid ($H_3PW_{12}O_{40} \cdot nH_2O$),
dodecatungstoboric acid ($H_5BW_{12}O_{40} \cdot nH_2O$),
octadecotungstodiphosporic acid ($H_6P_2W_{18}O_{62} \cdot 14H_2O$),
octadecotungstodiarsenic(V) acid ($H_6As_2W_{18}O_{62} \cdot 14H_2O$),
hexamolybdatohexatungstophosphoric acid ($H_3PMo_6W_6O_{40} \cdot nH_2O$).

Obviously, mixtures of heteropolyacids can also be removed. Frequently, the process according to the invention serves to remove dodecotungstophosphoric acid, dodecotungstosilicic acid and/or dodecomolybdatosilicic acid, since these are preferentially used as catalysts owing to their ready availability.

The process according to the invention is particularly preferably used for the purification of polymers in whose preparation processes the free heteropolyacids have been used as catalysts. However, it is also possible to separate off alkaline metal salts and/or alkaline earth metal salts of heteropolyacids.

The heteroatoms of the compound as described in claim 1 used to remove heteropoly compounds can therefore be main group and subgroup elements of the Periodic Table of the Elements. Examples of main group heteroelements are boron, silicon, germanium, tin, phosphorus, arsenic, antimony, selenium and tellurium. Examples of subgroup heteroelements are cerium, vanadium, chromium, molybdenum, tungsten, manganese and nickel.

For the purposes of this invention, "non-protic" is a compound whose $pKa \geq 20$.

By choosing suitable substituents, the compound serving for HPA precipitation can be optimally matched to the polymer to be purified or its solution. Furthermore, for an additional increase in the hydrolytic stability, compounds are preferred which have a reducing action, i.e. they can themselves be oxidized. These are compounds in which the heteroelement is not present in the highest oxidation state. Examples of heteroelement compounds used in the process according to the invention are: phosphites, such as triethyl phosphite, phosphonates, such as dimethyl methanephosphonate, phosphines, such as tributyl phosphine, phosphine oxides, such as tributylphosphine oxide, silanes, such as tetramethylsilane, triisopropylchlorosilane, methoxytrimethylsilane or tetrabutoxysilane, heteroelement-containing ethers, such as bis(trimethylsilyl) ether, boranes, such as trisborane, or tetraalkyltin compounds, such as tetrabutyltin.

The heteroelements present in these compounds are preferably those which are present in the respective HPA catalysts used, e.g. phosphorus in triethyl phosphite as heteroelement compound used for the precipitation and in dodecamolybdatophosphoric acid as catalyst. However, compounds whose heteroelement differs from that in the HPA employed can also be used, for example silicon in tetramethylsilane as heteroelement compound employed for the precipitation, with dodecatungstophosphoric acid used as catalyst.

To simplify the process according to the invention, heteroelement compounds which are liquid at room temperature are preferably used for the precipitation. Furthermore, the heteroelement compounds should advantageously be stable under the reaction conditions.

The amount by weight of the heteroelement compound to be used depends on the HPA content and on the content of other low-molecular weight compounds, such as monomer(s), chain termination reagent(s), solvent(s) etc. in the polymer phase to be purified, but is usually at least half as much as, frequently as much as up to twice as much as the total amount by weight of the other low-molecular weight compounds. Based on the amount of polyether, polyester and/or polyether ester, the amount of heteroelement compound should generally be 50% by weight or more, preferably 100% by weight or more.

If large amounts of low-molecular weight compounds are present together with the polymer to be purified, large amounts of heteroelement compound would also have to be added to precipitate the HPA. It can therefore be expedient to concentrate a polymer-containing mixture to a polymer content of at least 10, or preferably at least 50, % by weight or more, prior to addition of the heteroelement compound employed for precipitation.

With the addition according to the invention of the heteroelement compound, the majority of the HPA dissolved in the polymer phase precipitates out. It can be advantageous here to mix the polymer phase in a suitable manner, for example by conventional stirring. Temperatures and pressures at which the process can be carried out simply are chosen for the HPA removal. The temperatures employed should not be too high, since the HPA solubility in the polymer phase increases with increasing temperature; usually, temperatures from 25° to 60° C. are chosen. The mixture can stand from 0.1 to 200 hours to complete the precipitation, 0.5 hours usually being sufficient. The formation of emulsions is frequently observed. In this case, the phase separation can be accelerated by suitable measures (e.g. use of a coalescing filter).

The majority of the HPA dissolved in the polyether, polyester arid/or polyether ester phase is successfully separated off by means of the process according to the invention. The HPA usually arises in the liquid phase, which can be recycled directly to the polymerization stage.

If, for example, the abovementioned THF/polyTHF phase, which is obtained in the THF polymerization in the presence of water and $H_3PW_{12}O_{40}$ as catalyst, is admixed with half the amount by weight of tetramethylsilane, the majority of the dissolved HPA separates out in the form of a liquid phase. The residual HPA content in the THF/polyTHF/tetramethylsilane phase decreases to 5 ppm here.

The processes proceeding in the precipitation of HPA by addition of the heteroelement compound have not yet been clarified in all details. A possible mechanism could be that the addition of the heteroatomic component greatly decreases the solubility of heteropoly compounds in the polymer phase by decreasing the polarity of same, so that they precipitate out from the polymer phase.

Polyethers, polyesters and polyether esters having an HPA content decreased as described above can be further purified by contacting them with a solid adsorbent, directly or in solution. Preference is given to the use of monomer/polymer mixtures which may still contain solvent. These mixtures can be used in the form in which they arise in HPA precipitation, or else in concentrated or dilute form. The amount of monomer advantageously present in the polymer phase should be at least 10% by weight, better 50% by weight or more.

The type of solid adsorbent is not restricted, provided that it can adsorb heteropoly compounds. Preference is given to activated carbons, aluminum oxides, oxides, hydroxides and carbonates of alkaline earth metals and rare earth metals and basic ion exchangers. The amount of adsorbent depends on the HPA content and can be 2 to 5000 times, preferably 10 to 1000 times, that of dissolved HPA. Generally, the use of larger amounts of solid adsorbent leads to a lower residual HPA content after the treatment.

The temperature in this purification step is not particularly restricted and should be selected in such a manner that the solution to be treated has a suitable viscosity. If a polyether having a mean molar mass of 1000 is used in pure form, the suitable temperature is usually from 20° to 150° C., preferably from 30° to 100° C.

If, after the treatment with a solid adsorbent, the purified polymer still contains monomer or solvent, they may be removed, for example, by distillation at atmospheric pressure or under reduced pressure, in which case a polymer having a very low HPA content can be obtained, which can be below 1 ppm, based on pure polyether, polyester and/or polyether ester. Therefore, polyethers, polyesters and/or polyether esters can be obtained in high purity in an economical manner by the process according to the invention.

The examples below illustrate the invention; all percentages for concentrations are by weight. The experiments were all performed under nitrogen. The heteropolyacids were quantitatively analyzed by x-ray fluorescence and atomic absorption.

EXAMPLE 1

A polymer phase was used which arose in the polymerization of tetrahydrofuran (THF) to give polytetrahydrofuran (polyTHF) in the presence of water using $H_3PW_{12}O_{40}$ as catalyst, and had the following composition: THF (77.3%), polyTHF (21.2%), $H_3PW_{12}O_{40}$ (1.2%), water (0.3%).

100 g of this mixture were admixed with 200 g of triethyl phosphite. After 30 hours, the majority of the previously dissolved $H_3PW_{12}O_{40}$ had precipitated out in the form of a liquid mixture and could be separated off. The THF/polyTHF/triethyl phosphite phase still had a residual content of 200 ppm of $H_3PW_{12}O_{40}$. The organic phase was then admixed with 20 g of activated carbon (Merck) and was shaken for 4 hours at room temperature. In the polyTHF which was obtained after separating off the activated carbon and concentration under reduced pressure, the $H_3PW_{12}O_{40}$ content was in all cases below 1 ppm.

EXAMPLE 2

A polymer phase was used, which arose in the polymerization of caprolactone to give polycaprolactone in the presence of water using $H_3PW_{12}O_{40}$ as catalyst, and had the following composition: polycaprolactone (98.2%), $H_3PW_{12}O_{40}$ (1.8%). 100 g of this mixture were admixed with 200 g of triethyl phosphite. After 30 hours, the majority of the previously dissolved $H_3PW_{12}O_{40}$ had precipitated out in the form of a liquid mixture and was separated off. The THF/polycaprolactone/triethyl phosphite phase still had a residual content of 420 ppm of $H_3PW_{12}O_{40}$. The organic phase was then admixed with 20 g of activated carbon (Merck) and shaken for 4 hours at room temperature. The $H_3PW_{12}O_{40}$ content in the polycaprolactone obtained after separating off the activated carbon and concentration under reduced pressure was below 1 ppm.

EXAMPLES 3–11

In each of Examples 3–11, 100 g of a THF/polyTHF/HPA solution whose composition is specified in Table I was used. The heteroatom-containing compound indicated as "purification compound" was added to this mixture and the residual HPA content in the mixture was determined after 50 hours. All samples were then admixed with 20 g of activated carbon, shaken for 4 hours at room temperature and then concentrated at 10 mbar/140° C. Analysis of the polyTHF thus obtained gave a residual HPA content of less than 1 ppm.

TABLE I

| Example | Composition of the solution | | | Purification compound | | Residual HPA content [ppm] |
|---|---|---|---|---|---|---|
| | poly-THF [% by weight] | THF [% by weight] | HPA [% by weight] | Type | Amount [g] | |
| 3 | 77.3 | 21.2 | 1.2 | tetramethylsilane | 50 | 5 |
| 4 | 77.3 | 21.2 | 1.2 | tetraethylsilane | 50 | 5 |
| 5 | 77.3 | 21.2 | 1.2 | tetrabutyltin | 50 | 5 |
| 6 | 77.3 | 21.2 | 1.2 | tetrabutoxysilane | 50 | 5 |
| 7 | 77.3 | 21.2 | 1.2 | trisdimethylaminoborane | 50 | 5 |
| 8 | 77.3 | 21.2 | 1.2 | dimethyl methanephosphonite | 50 | 5 |
| 9 | 77.3 | 21.2 | 1.2 | tributylphosphine oxide | 50 | 5 |
| 10 | 77.3 | 21.2 | 1.2 | triisopropylchlorosilane | 50 | 5 |
| 11 | 77.3 | 21.2 | 1.2 | bis(trimethylsilyl) ether | 200 | 8 |

We claim:

1. A process for removing heteropoly compounds from heteropoly compound-contaminated polyethers, polyesters or polyether esters, which comprises admixing the polymer or a solution of the polymer with a compound which contains at least one heteroatom which is selected from the group consisting of central atoms of heteropolyacids, is non-protic and is of a polarity that leads to the heteropoly compounds separating out in a separate phase, and separating off the precipitated heteropoly compound phase.

2. A process as defined in claim 1, wherein the heteroatom in the compound containing at least one heteroatom is selected from the group consisting of B, Si, Ge, Sn, P, As, Sb, Se, Te, Ce, V, Cr, Mo, W, Mn and Ni.

3. A process as defined in claim 2, wherein the heteroatom is selected from the group consisting of B, Si or P.

4. A process as defined in claim 1, wherein the compound containing at least one heteroatom is not present in its highest oxidation state.

5. A process as defined in claim 1, wherein an amount by weight of the compound containing at least one heteroatom is added which is at least half as much as the amount by weight of other low-molecular weight compounds present or is at least 50% of the amount by weight of polymer present.

6. A process as defined in claim 1, wherein a solution of the polymer is concentrated to a polymer content of at least 10% by weight, preferably at least 50% by weight, before it is admixed with the compound containing at least one heteroatom.

7. A process as defined in claim 1, wherein, after separating off the heteropoly compound phase, the polymer is contacted with a solid adsorbent which is capable of adsorbing heteropoly compounds.

8. A process as defined in claim 1, wherein the solid adsorbent used is one, or a mixture of a plurality, selected from the group consisting of activated carbons, aluminum oxides, alkaline earth metal oxides and rare earth metal oxides, hydroxides and carbonates and basic ion exchangers.

9. A process as defined in claim 1, wherein, after removing the heteropoly compounds, the polymer is obtained by separating off monomers, chain termination reagents, any solvents added and other low-boiling compounds.

10. A process as defined in claim 1, wherein a polyether containing polyoxytetramethylene groups is used.

11. A process as defined in claim 1, wherein the heteropoly compound phase separated off is reused as polymerization catalyst.

12. The process as defined in claim 6, wherein the polymer content is at least 50% by weight.

* * * * *

UNITED STATES PATENT AND TRADEMARK OFFICE
CERTIFICATE OF CORRECTION

PATENT NO.: 5,824,769

DATED: October 20, 1998

INVENTOR(S): WEYER et al.

It is certified that error appears in the above-identified patent and that said Letters Patent is hereby corrected as shown below:

Col. 8, claim 3, line 6, "or" should be --and--.

Coo. 8, claim 6, line 17, delete "preferably at least 50% by weight,".

Signed and Sealed this

Twelfth Day of January, 1999

Attest:

Attesting Officer

*Acting Commissioner of Patents and Trademarks*